United States Patent
Ressel et al.

(10) Patent No.: US 9,850,263 B2
(45) Date of Patent: Dec. 26, 2017

(54) PROCESS FOR PREPARING PHOSPHORUS CONTAINING CYANOHYDRINS

(71) Applicant: BAYER CROPSCIENCE AKTIENGESELLSCHAFT, Monheim am Rhein (DE)

(72) Inventors: Hans-Joachim Ressel, Hattersheim (DE); Kilian Tellman, Cologne (DE); Mark James Ford, Wiesbaden-Breckenheim (DE); Martin Littmann, Leverkusen (DE); Friedrich August Muehlthau, Kelkheim-Fischbach (DE); Guenter Schlegel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/310,566

(22) PCT Filed: May 8, 2015

(86) PCT No.: PCT/EP2015/060211
§ 371 (c)(1),
(2) Date: Nov. 11, 2016

(87) PCT Pub. No.: WO2015/173146
PCT Pub. Date: Nov. 19, 2015

(65) Prior Publication Data
US 2017/0081349 A1 Mar. 23, 2017

(30) Foreign Application Priority Data
May 13, 2014 (EP) .................... 14168134

(51) Int. Cl.
*C07F 9/32* (2006.01)
*C07F 9/30* (2006.01)

(52) U.S. Cl.
CPC ............ *C07F 9/3211* (2013.01); *C07F 9/301* (2013.01)

(58) Field of Classification Search
CPC .............................. C07F 9/3211; C07F 9/301
See application file for complete search history.

(56) References Cited

U.S. PATENT DOCUMENTS

| | | |
|---|---|---|
| 3,850,976 A | 11/1974 | Shibuya et al. |
| 3,914,345 A | 10/1975 | Kleiner et al. |
| 4,168,963 A | 9/1979 | Rupp et al. |
| 4,336,206 A | 6/1982 | Muendnich et al. |
| 4,474,711 A | 10/1984 | Keliner et al. |
| 4,485,052 A | 11/1984 | Kleiner et al. |
| 4,521,348 A * | 6/1985 | Finke .................... C07F 9/301 558/137 |
| 4,599,207 A | 7/1986 | Lachhein et al. |
| 4,839,105 A | 6/1989 | Kleiner |
| 5,128,495 A | 7/1992 | Scheffel et al. |
| 6,359,162 B1 | 3/2002 | Willms |

FOREIGN PATENT DOCUMENTS

| | | |
|---|---|---|
| CN | 101830926 A | 9/2010 |
| CN | 102372739 A | 3/2012 |
| CN | 102399240 A | 4/2012 |
| DE | 2302523 A1 | 8/1974 |
| DE | 3047024 A1 | 7/1982 |
| EP | 0011245 A1 | 5/1980 |
| EP | 0029168 A1 | 5/1981 |
| EP | 0127877 A2 | 12/1984 |
| EP | 0546566 A1 | 6/1993 |

OTHER PUBLICATIONS

International Search Report of International Patent Application No. PCT/EP2015/060211 dated Jun. 9, 2015.
Serge R. Piettre, Simple and Efficient Synthesis of 2,2-Disubstituted-1,1-Difluorophosphonates and Phosphonothioates Tetrahedron Letters. (1996) vol. 37, No. 13: 2233-2236.

* cited by examiner

*Primary Examiner* — Michael Barker
*Assistant Examiner* — Amanda L Aguirre
(74) *Attorney, Agent, or Firm* — McBee Moore Woodward & Vanik IP, LLC

(57) ABSTRACT

The present invention relates primarily to a process for preparing certain phosphorus-containing cyanohydrins of the formula (I), and also to certain phosphorus-containing cyanohydrins per se and to their use for the preparation of glufosinate and/or glufosinate salts. The present invention further relates to certain mixtures particularly suitable for preparing the phosphorus-containing cyanohydrins of the formula (I).

13 Claims, No Drawings

PROCESS FOR PREPARING PHOSPHORUS CONTAINING CYANOHYDRINS

CROSS REFERENCE TO RELATED APPLICATIONS

This application is a §371 National State Application of PCT/EP2015/060211, filed May 8, 2015, which claims priority to European Application Nos. 14168134.6 filed May 13, 2014.

BACKGROUND OF THE INVENTION

Field of the Invention

The present invention relates primarily to a process for preparing certain phosphorus-containing cyanohydrins of the formula (I) defined below, and also to certain phosphorus-containing cyanohydrins per se and to their use for the preparation of glufosinate and/or glufosinate salts. The present invention further relates to certain mixtures particularly suitable for preparing the phosphorus-containing cyanohydrins of the formula (I) defined below.

Description of Related Art

Phosphorus-containing cyanohydrins are useful intermediates in a variety of subject fields, more particularly for the production of biologically active substances which can be used in the pharmaceutical and/or agrochemical sector.

U.S. Pat. No. 4,168,963 describes diverse phosphorus-containing compounds with herbicidal activity, of which, in particular, phosphinothricin (2-amino-4-[hydroxy(methyl)phosphinoyl]butanoic acid; common name: glufosinate) and its salts have acquired commercial importance in the agrochemistry (agricultural chemistry) sector.

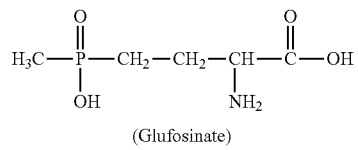

(Glufosinate)

Methods for producing intermediates for the synthesis of phosphorus-containing compounds of this kind with herbicidal activity, more particularly glufosinate, are described in U.S. Pat. No. 4,521,348, DE 3047024, U.S. Pat. No. 4,599,207 and U.S. Pat. No. 6,359,162B1, for example.

CN 102372739A describes a process for preparing glufosinate by reacting (3-cyano-3-hydroxypropyl)-methylphosphinic acid with carbon dioxide, ammonia and water.

CN 102399240A discloses processes for preparing glufosinate and glufosinate analogs, the starting materials therein including $PCl_3$, $CH_3MgCl$ and certain trialkyl esters of phosphorous acid. The dialkyl methylphosphonates and alkyl methylphosphinates prepared therefrom are subsequently reacted therein by Michael addition and further reaction steps to form glufosinate and glufosinate analogs.

CN 101830926A relates to the preparation of dialkylmetal phosphinates and to the use thereof as flame retardants. In the process described, alkyl phosphinates are reacted with terminal olefins, the reactions including that of monobutyl methanephosphinate with cyclohexene.

The processes from the prior art for preparing phosphorus-containing cyanohydrins have disadvantages: for example, an inadequate yield of phosphorus-containing cyanohydrins, an excessive fraction of co-products or secondary products, an excessive cost and complexity in purifying and/or isolating the phosphorus-containing cyanohydrins, and/or reaction conditions which are too harsh or too difficult in terms of process and/or equipment.

SUMMARY

It was an object of the present invention, therefore, to find a process for preparing phosphorus-containing cyanohydrins that affords the phosphorus-containing cyanohydrins in a very good yield.

The process ought preferably to fulfil simultaneously one, two or more, or all of the following aspects (i) to (iv):
(i) maximum ease of implementation in terms of process and/or equipment;
(ii) mild reaction conditions;
(iii) very low fraction of secondary products (that are difficult to remove);
(iv) extremely simple purification and/or isolation of the phosphorus-containing cyanohydrins.

This object is fulfilled by the process of the invention as described hereinafter.

The present invention provides a process for preparing phosphorus-containing cyanohydrins of the formula (I)

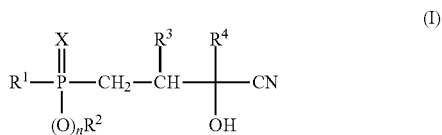

characterized in that a compound of the formula (II)

is reacted with a cyanohydrin of the formula (III)

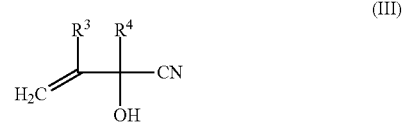

at a temperature in the range from 50 to 105° C., preferably at a temperature in the range from 60 to 95° C., more preferably at a temperature in the range from 65 to 90° C., where in each case:
$R^1$ is $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl,
$R^2$ is $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl,
$R^3$ and $R^4$ are in each case independently of one another hydrogen, $(C_1-C_4)$-alkyl, phenyl or benzyl,
X is oxygen or sulphur, and
n is 0 or 1.

DETAILED DESCRIPTION OF A PREFERRED EMBODIMENT

DE 3047024 describes in principle the reaction of compounds of the formula (II) with compounds of the formula (III) to form compounds of the formula (I), but in an unsatisfactory yield, which is inadequate in particular on the industrial or plant scale. By way of example, DE 3047024 describes the reaction of monoisobutyl methanephosphonate with acrolein cyanohydrin with addition of a catalytic amount of a "peroctoate" radical initiator at a temperature of 120-130° C. The yield after distillation there was 79% of theory.

The cyanohydrins of the formula (III) have a significantly higher reactivity than the corresponding compounds which have an O-acetyl group instead of the free hydroxyl group, of the kind used in U.S. Pat. No. 4,521,348 or U.S. Pat. No. 4,599,207, for example.

With the process of the invention, in which the reaction temperature is held within the temperature range defined in accordance with the invention, and in which preferably radical initiators of the formula (IV) defined below are used, the phosphorus-containing cyanohydrins of the formula (I) are obtained in significantly better yield and generally in higher purity.

The compounds of the formula (III) used in the process of the invention do not have an O-acetyl group, and the further glufosinate preparation process of the invention described below, in contrast to the processes described in U.S. Pat. No. 4,521,348 or U.S. Pat. No. 4,599,207, does not produce any acetic acid or acetic acid derivatives as accompanying components or co-products.

It has further emerged that in the process of the invention for preparing the compound of the formula (I) (and also the compound of the formula (Ia) or (Ib) defined below), the quality of the unreacted and recovered—that is, recycled—amount of the compound of the formula (II) (or of the formula (IIa) or (IIb) defined below) after reaction has taken place is better than in the processes known from the literature where, rather than the cyanohydrins of the formula (III), the corresponding O-acetylated cyanohydrins are used.

Recovered (recycled) quantities of the compound of the formula (II) from the processes known from the literature that use, rather than the cyanohydrins of the formula (III), the corresponding O-acetylated cyanohydrins customarily contain marked fractions (about 5 wt %) of acetic acid, which are impossible to remove without considerable distillative cost and complexity. But residual amounts of acetic acid inhibit or slow down the radical reaction, rendering it disadvantageous to return the recovered (recycled) quantities of the compound of the formula (II) into the radical reaction and to use them again in that reaction.

Overall, in the process of the invention, and in the further processes of the invention described below for the preparation of glufosinate, fewer unwanted secondary components are formed, and so the processes of the invention are more efficient and more energy-saving.

The respective alkyl radicals of the radicals $R^1$, $R^2$, $R^3$ and $R^4$ may in each case be straight-chain or branched-chain (branched) in the carbon scaffold.

The expression "$(C_1-C_4)$-alkyl" here is the abbreviated notation for an alkyl radical having 1 to 4 carbon atoms, therefore encompassing the radicals methyl, ethyl, 1-propyl, 2-propyl, 1-butyl, 2-butyl, 2-methylpropyl or tert-butyl. Correspondingly, general alkyl radicals with a greater stated range of C atoms, as for example "$(C_1-C_6)$-alkyl", also encompass straight-chain or branched alkyl radicals having a greater number of C atoms, i.e., according to example, the alkyl radicals also having 5 and 6 C atoms.

"Halogen" pertains preferably to the group consisting of fluorine, chlorine, bromine and iodine. Haloalkyl, haloaryl, haloaralkyl and halocycloalkyl denote alkyl, aryl, aralkyl and cycloalkyl, respectively, that are partly or wholly substituted by identical or different halogen atoms, preferably from the group of fluorine, chlorine and bromine, more particularly from the group of fluorine and chlorine. Thus, for example, haloalkyl encompasses monohaloalkyl (=monohalogenoalkyl), dihaloalkyl (=dihalogenoalkyl), trihaloalkyl (=trihalogenoalkyl), or else perhaloalkyl, such as, for example, $CF_3$, $CHF_2$, $CH_2F$, $CF_3CF_2$, $CH_2FCHCl$, $CCl_3$, $CHCl_2$, $CH_2CH_2Cl$. Corresponding comments apply to the other radicals substituted by halogen.

Suitable and preferred compounds of the formula (II) include the following: methanephosphonous acid mono($C_1$-$C_6$)-alkyl esters, monododecyl methanephosphonate, monophenyl methanephosphonate; ethane-phosphonous acid mono($C_1$-$C_6$)-alkyl esters, monododecyl ethanephosphonate, monophenyl ethanephosphonate; propanephosphonous acid mono($C_1$-$C_6$)-alkyl esters, monododecyl propanephosphonate, monophenyl propanephosphonate; butanephosphonous acid mono($C_1$-$C_6$)-alkyl esters, monododecyl butanephosphonate, monophenyl butanephosphonate; phenylphosphonous acid mono($C_1$-$C_6$)-alkyl esters, monododecyl phenylphosphonate, monophenyl phenylphosphonate; benzylphosphonous acid mono-($C_1$-$C_6$)-alkyl esters, monododecyl benzylphosphonate, monophenyl benzylphosphonate; methylthio-phosphonous acid mono($C_1$-$C_6$)-alkyl esters, monododecyl methylthiophosphonate, monophenyl methylthiophosphonate; dimethylphosphine oxide, diethylphosphine oxide, dipropylphosphine oxide, dibutyl-phosphine oxide, diphenylphosphine oxide, methylphenylphosphine oxide, dibenzylphosphine oxide, dimethylphosphine sulphide, and diphenylphosphine sulphide.

The preparation of the compounds of the formula (II) is known to the skilled person and can take place in accordance with processes known from the literature (e.g. U.S. Pat. No. 3,914,345; U.S. Pat. No. 4,474,711; U.S. Pat. No. 4,485,052; U.S. Pat. No. 4,839,105; U.S. Pat. No. 5,128,495).

Suitable and preferred cyanohydrins of the formula (III) include the following: acrolein cyanohydrin, methacrolein cyanohydrin, ethacrolein cyanohydrin, and phenyl vinyl ketone cyanohydrin.

The preparation of the cyanohydrins of the formula (III) is known to the skilled person and can take place in accordance with processes known from the literature (e.g. from U.S. Pat. No. 3,850,976 or U.S. Pat. No. 4,336,206).

For the process of the invention, the following is preferably the case:

$R^3$ and $R^4$ are in each case independently of one another hydrogen or methyl, and/or X is oxygen, and/or n is 1.

The process of the invention relates preferably to the preparation of phosphorus-containing cyanohydrins of the formula (Ia)

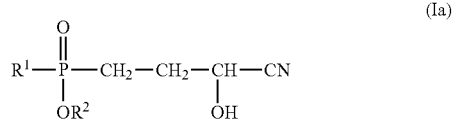

characterized in that a compound of the formula (IIa)

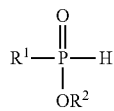
(IIa)

is reacted with acrolein cyanohydrin of the formula (IIIa)

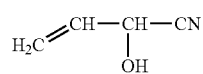
(IIIa)

at a temperature in the range from 50 to 105° C., preferably at a temperature in the range from 60 to 95° C., more preferably at a temperature in the range from 65 to 90° C., where in each case:
$R^1$ is $(C_1\text{-}C_6)$-alkyl, $(C_1\text{-}C_6)$-haloalkyl, $(C_6\text{-}C_8)$-aryl, $(C_6\text{-}C_8)$-haloaryl, $(C_7\text{-}C_{10})$-aralkyl, $(C_7\text{-}C_{10})$-haloaralkyl, $(C_5\text{-}C_8)$-cycloalkyl or $(C_5\text{-}C_8)$-halocycloalkyl,
$R^2$ is $(C_1\text{-}C_6)$-alkyl, $(C_1\text{-}C_6)$-haloalkyl, $(C_6\text{-}C_8)$-aryl, $(C_6\text{-}C_8)$-haloaryl, $(C_7\text{-}C_{10})$-aralkyl, $(C_7\text{-}C_{10})$-haloaralkyl, $(C_5\text{-}C_8)$-cycloalkyl or $(C_5\text{-}C_8)$-halocycloalkyl.

Preferably in each case:
$R^1$ is $(C_1\text{-}C_4)$-alkyl or $(C_1\text{-}C_4)$-haloalkyl, preferably methyl or ethyl,
$R^2$ is $(C_1\text{-}C_6)$-alkyl or $(C_1\text{-}C_6)$-haloalkyl, preferably $(C_3\text{-}C_6)$-alkyl, in turn preferably $C_4$-alkyl or $C_5$-alkyl.

More preferably in each case:
$R^1$ is methyl,
$R^2$ is $C_4$-alkyl or $C_5$-alkyl, preferably n-butyl or n-pentyl, i.e. particular preference is given to using compounds of the formula (IIb)

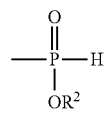
(IIb)

where $R^2$ is n-butyl or n-pentyl.

The process of the invention is preferably carried out under conditions in which free radicals are formed.

The reaction of the compounds of the formula (II) and (III) or (IIa) and (IIIa) to give the compounds of the formula (I) or (Ia), respectively, in a process of the invention takes place preferably with the aid of a radical-forming radiation source (such as UV, gamma or X-rays) or in the presence of one or more radical-forming substances.

For the purposes of the process of the invention, preference is given to using radical-forming substances, more preferably radical initiators of the formula (IV) defined below:

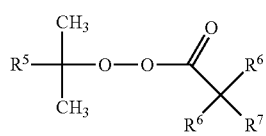
(IV)

where
$R^5$ is methyl, ethyl, 2,2-dimethylpropyl or phenyl,
$R^6$ independently at each occurrence is $(C_1\text{-}C_{10})$-alkyl, preferably $(C_1\text{-}C_6)$-alkyl, more preferably $(C_1\text{-}C_4)$-alkyl,
and
$R^7$ hydrogen or $(C_1\text{-}C_{10})$-alkyl, preferably hydrogen or $(C_1\text{-}C_6)$-alkyl, more preferably hydrogen or $(C_1\text{-}C_4)$-alkyl.

The radical initiators of the formula (IV) are known per se and some of them are available commercially.

The radical initiators of the formula (IV) are preferably selected from the group consisting of tert-butyl peroxypivalate, tert-amyl peroxypivalate, tert-butyl peroxyneodecanoate, 1,1,3,3-tetramethylbutyl peroxyneodecanoate, tert-butylperoxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate, and mixtures thereof.

The radical initiators of the formula (IV) are preferably selected from the group consisting of tert-butylperoxyneodecanoate, 1,1,3,3-tetramethylbutyl peroxyneodecanoate, tert-butylperoxy-2-ethylhexanoate, 1,1,3,3-tetramethylbutyl peroxy-2-ethylhexanoate, cumyl peroxyneodecanoate, and mixtures thereof, more preferably in turn 1,1,3,3-tetramethylbutyl peroxyneodecanoate, tert-butyl peroxyneodecanoate and/or tert-butylperoxy-2-ethylhexanoate.

The radical initiators stated as preferred, in particular, permit a very good reaction regime under mild reaction conditions, more particularly within the temperature range stated as preferred, thereby allowing the desired phosphorus-containing cyanohydrins of the formula (I) and (Ia) to be obtained in high yields and high purity.

Preference is given to using a total of 0.1 to 10 mol %, more preferably 0.25 to 7 mol %, even more preferably 0.5 to 7 mol %, especially preferably 0.5 to 5 mol %, of radical initiators of the formula (IV), based on the total amount of cyanohydrin of the formula (III) or (IIIa) that is used.

The radical initiator of the formula (IV), or a mixture of radical initiators of the formula (IV), may be mixed together with the cyanohydrin of the formula (III) or (IIIa), and the mixture metered in—that is, added under dosage control—to the initially introduced compound of the formula (II) or (IIa). Alternatively, the radical initiator or a mixture of radical initiators of the formula (IV) may also be mixed with the phosphorus-containing reactant (II) or (IIa) or added, under dosage control, in pure form simultaneously separately alongside the cyanohydrin of the formula (III) or (IIIa).

The radical initiator or a mixture of radical initiators of the formula (IV) is preferably mixed with the phosphorus-containing reactant (II) or (IIa) or may also be added under dosage control in pure form simultaneously separately alongside the cyanohydrin of the formula (III) or (IIIa). Alternatively, the radical initiator of the formula (IV), or a mixture of radical initiators of the formula (IV), may also be mixed together with the cyanohydrin of the formula (III) or (IIIa), and the mixture metered in—that is, added under dosage control—to the initially introduced compound of the formula (II) or (IIa).

Where a "portion" is referred to in the observations hereinafter, only part of the total amount used in the process of the invention is used in the procedure defined at that particular point.

The process of the invention can be carried out such that the radical initiator or initiators of the formula (IV), or a portion of the radical initiator or initiators of the formula (IV), is premixed with a portion or the entirety of the compound (III) or (IIIa) ("mixture IV+III"), and this mixture, i.e. "mixture IV+III", is metered into the reaction vessel.

The process of the invention is preferably carried out such that
compound (III) or (IIIa) is premixed with a portion of the compound (II) or (IIa) ("mixture III+II"),
spatially separately therefrom (i.e. in a separate container), a portion of the compound (II) or (IIa) is premixed with the radical initiator (IV) ("mixture II+IV"),
and these two mixtures, i.e. "mixture III+II" and "mixture II+IV", are metered simultaneously into the reaction vessel.

With the preferred procedures below, the phosphorus-containing cyanohydrins of the formula (I) or (Ia) are obtained particularly effectively and in even better yield.

The process of the invention is preferably carried out, accordingly, such that the radical initiator or initiators of the formula (IV) or a portion of the radical initiator or initiators of the formula (IV) is or are premixed with a portion or the entirety of the compound (II) or (IIa) ("mixture IV+II"), and this mixture, i.e. "mixture IV+II", is metered simultaneously with and separately from the compound of the formula (III) or (IIIa) into the reaction vessel.

Compound of the formula (III) or (IIIa) here is preferably metered into the reaction vessel from a separate container that constitutes a separate construction.

In the case of the batch mode, and depending in that case on the batch size, the simultaneous metering in each of the above mentioned procedures lasts preferably for longer than 30 minutes, more preferably 30 minutes to 20 hours, very preferably 1 to 12 hours.

The above-defined mixtures "mixture IV+III", "mixture IV+II", "mixture III+II", and "mixture II+IV" are likewise provided by the present invention.

The present invention consequently also relates to a mixture selected from the group consisting of
mixture comprising one or more compounds of the formula (IV) and one or more compounds of the compound (III) formula,
mixture comprising one or more compounds of the formula (IV) and one or more compounds of the compound (II) formula,
mixture comprising one or more compounds of the formula (III) and one or more compounds of the compound (II) formula, wherein such a mixture preferably contains no compound of the above-defined formula (IV) and/or no compound of the above-defined formula (I),
wherein the compounds of the formula (II), (III) and (IV) each have the structure defined above, preferably in each case a structure defined above as preferred or particularly preferred.

The present invention preferably relates to a mixture selected from the group consisting of
mixture comprising one or more compounds of the formula (IV) and one or more compounds of the compound (III) formula,
mixture comprising one or more compounds of the formula (IV) and one or more compounds of the compound (II) formula,
wherein the compounds of the formula (II), (III) and (IV) each have the structure defined above, preferably in each case a structure defined above as preferred or particularly preferred.

For the mixtures of the invention it is preferably the case that the compounds of the formula (II) and the compounds of the formula (III) are selected from the group of the compounds of the formula (IIa) and from the group of the compounds of the formula (IIIa), with the compounds of the formula (IIa) and/or (IIb) and also (IIIa) defined above as preferred being preferred in turn.

Preferred mixtures of the invention comprise or consist of
one or more radical initiators of the formula (IV) selected from the group consisting of tert-butyl peroxypivalate, tert-amyl peroxypivalate, tert-butyl peroxyneodecanoate, 1,1,3,3-tetramethylbutyl peroxyneodecanoate, tert-butylperoxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, and cumyl peroxypivalate,
and
a compound of the formula (III), preferably of the formula (IIIa).

Preferred mixtures of the invention comprise or consist of
one or more radical initiators of the formula (IV) selected from the group consisting of tert-butyl peroxypivalate, tert-amyl peroxypivalate, tert-butyl peroxyneodecanoate, 1,1,3,3-tetramethylbutyl peroxyneodecanoate, tert-butylperoxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, and cumyl peroxypivalate,
and
a compound of the formula (II), preferably of the formula (IIa).

The process of the invention enables the preparation of the phosphorus-containing cyanohydrins of the formula (I) or (Ia) under mild reaction conditions, thereby giving the phosphorus-containing cyanohydrins of the formula (I) or (Ia) in very good yields, which are significantly higher than as described in U.S. Pat. No. 4,521,348 or DE 3047024.

Accordingly, when the process of the invention is implemented, disproportionation of reactants of the formula (II) or (IIa), for example, is significantly lessened or largely prevented. Moreover, when the process of the invention is implemented, polymerization of the compounds of the formula (III) or (IIIa) is significantly lessened or largely prevented.

It has further been found that by premixing (parts) of the reactants of the formulae (II) and (III) or (IIa) and (IIIa), the polymerization tendency of compounds of the formula (III) or (IIIa) can be reduced still further.

In the context of the process of the invention it is advantageous to use the cyanohydrins of the formula (III) or (IIIa) in a very high purity. The cyanohydrins of the formula (III) or (IIIa) are preferably used in a purity of greater than or equal to 90 wt %, more preferably of greater than or equal to 92 wt %.

In the context of the process of the invention it is advantageous to stabilize the cyanohydrins of the formula (III) or (IIIa) with one or more acids, with preferably a pH in the range of 2-4 (measured at 25° C.) being established. The stabilizing acid used in this case may be, for example, phosphoric acid, polyphosphoric acid and/or acetic acid.

The phosphorus-containing cyanohydrins of the formula (I) or (Ia) that are formed may be used as starting materials for the synthesis of phosphorus-containing amino acids such as, for example, glufosinate (a synthesis route of this kind is described in more detail later on below). Another advantage of using cyanohydrins of the formula (III) or (IIIa) is therefore that it removes the need to introduce a protecting group for the OH group in the compounds of the formula (I) or (Ia) and (III) or (IIIa), and so makes the synthesis more simple overall.

In order to avoid unwanted secondary reactions and hence to achieve high yields, moreover, it is advantageous to use the phosphorus-containing reactant (II) or (IIa) in a molar excess, relative to the cyanohydrin of the formula (III) or (IIIa).

In the process of the invention, the molar ratio of the total amount of the phosphorus-containing reactant (II) or (IIa) used to the total amount of the cyanohydrin of the formula (III) or (IIIa) used is preferably in the range from 3:2 to 8:1, more preferably in the range from 2:1 to 6:1, more preferably still in the range from 5:2 to 5:1, very preferably in the range from 2.8:1 to 4.0:1.

The process of the invention can be carried out either in batch mode or in continuous mode (i.e. continuous operating regime).

The process of the invention is carried out preferably with inertizing, more preferably in an inert gas atmosphere. Preferred inert gases in this case are nitrogen and argon.

It is further possible to carry out the process of the invention under superatmospheric pressure or under reduced pressure.

The process of the invention can be carried out in a diluent.

As diluents it is possible in principle to use a variety of organic solvents, preferably toluene, xylene, chlorobenzene, dichlorobenzene, dimethylformamide (DMF), dimethylacetamide, N-methyl-2-pyrrolidone (NMP), or mixtures of these organic solvents. The process of the invention is preferably carried out without such solvents.

It may, however, be advantageous to carry out the process of the invention in reaction product of the formula (I) or (Ia), already formed beforehand, as diluent.

It may be advantageous to carry out the process of the invention in the reactant of the formula (II) or (IIa) as diluent, in which case preferably a portion of the reactant of the formula (II) or (IIa) is introduced as an initial charge to the reaction vessel or reactor.

Particularly in the case of continuous mode, it is advantageous to carry out the process of the invention in reaction product of the formula (I) or (Ia), already formed beforehand, or in a mixture of reaction product of the formula (I) or (Ia) and reactant of the formula (II) or (IIa), as diluent.

The yields according to the process of the invention amount regularly to 90-98%, based on the component of the formula (III) or (IIIa), and regularly to 88-96%, based on the component of the formula (II) or (IIa).

The purity of the products after purification, for example after distillative removal of the excess of component (II) or (IIa), amounts regularly to 90% to 96%. The recovered excess of the starting compound (II) can be used subsequently without further purification in the same reaction again.

In a further aspect, the present invention relates to particular phosphorus-containing cyanohydrins of the formula (Ib)

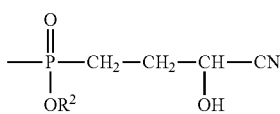

(Ib)

where $R^2$ is either n-butyl or n-pentyl, preferably n-butyl.

In our own investigations it has emerged that these two compounds can be prepared to particularly good effect with the process of the invention, and that these two compounds can be used with particular advantage in the further reaction to give corresponding active agrochemical ingredients, preferably to give compounds with herbicidal activity, and more particularly for the preparation of glufosinate and its salts.

This is true especially of the compound of the formula (Ib) where $R^2$=n-butyl, which is obtained according to the process of the invention by reacting the phosphorus-containing reactant (IIa) where $R^1$=methyl and $R^2$=n-butyl with acrolein cyanohydrin of the formula (IIIa).

Especially preferred, therefore, is the following compound (Ib-nBu):

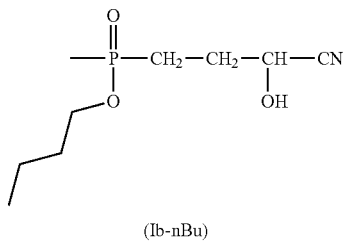

(Ib-nBu)

Accordingly, the present invention also relates to the use of the two phosphorus-containing cyanohydrins of the formula (Ib) for preparing glufosinate and/or glufosinate salts.

Glufosinate salts in the context of the present invention are preferably ammonium salts, phosphonium salts, sulphonium salts, alkali metal salts and alkaline earth metal salts of glufosinate.

Especially preferred in the context of the present invention are glufosinate, glufosinate-sodium and glufosinate-ammonium.

The reaction of the phosphorus-containing cyanohydrins of the formula (Ib) to form glufosinate and its salts may take place in analogy to the processes described from the prior art identified above.

In a further aspect, the present invention relates to the preparation of glufosinate and/or glufosinate salts

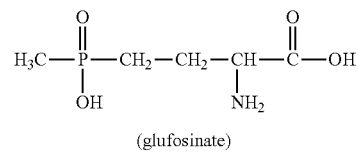

(glufosinate)

characterized by reaction of a compound of the formula (Ib), by the following step:
reaction of a compound of the formula (IIb)

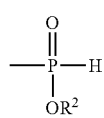

(IIb)

where $R^2$ is n-butyl or n-pentyl
with acrolein cyanohydrin of the formula (IIIa)

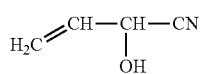

where the reaction of (IIb) with (IIIa) takes place preferably according to the process of the invention described above.

The process for preparing glufosinate and/or glufosinate salts takes place further preferably by reaction of a compound of the formula (Ib) with $NH_3$ to give compound (V)

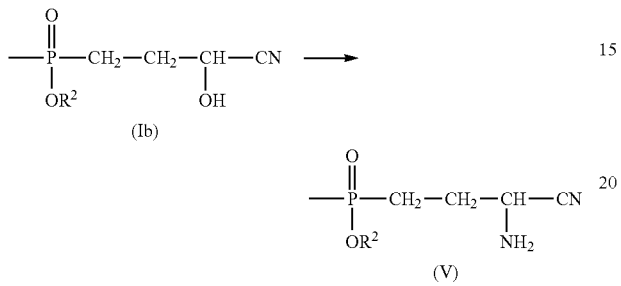

where $R^2$ in each case is n-butyl or n-pentyl, preferably n-butyl,
and subsequent hydrolysis of compound (V) to give glufosinate and/or its salts.

Glufosinate or glufosinate salt obtained by means of this process, preferably glufosinate-sodium salt or glufosinate-ammonium salt, is relatively easy to purify and to isolate. One reason for this is that fewer co-products and secondary products are produced in the processes of the invention, in comparison for example to the processes of U.S. Pat. No. 4,521,348 or U.S. Pat. No. 4,599,207.

With a view to what has been said above, therefore, the invention also relates to the new compounds of the formula (AMN)

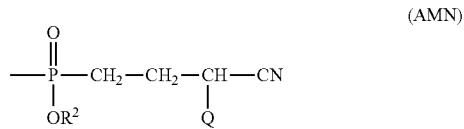

where
Q is either OH or $NH_2$,
$R^2$ is either n-butyl or n-pentyl, preferably n-butyl,
and also to their use for preparing glufosinate and/or glufosinate salts, more particularly glufosinate, glufosinate-sodium and glufosinate-ammonium.

EXAMPLES

Unless otherwise indicated, all figures are given by weight.

Example 1: Acrolein Cyanohydrin (Not Subject Matter of the Present Invention)

100 g (0.791 mol) of acrolein cyanohydrin acetate (99% purity) (obtainable for example as described in U.S. Pat. No. 4,336,206) were mixed with 300 ml of dry methanol, with inertizing using nitrogen, and the mixture was stirred at 20° C. for 6 days with 60 g of dried, previously activated* ion exchanger (Amberlyst 15, Rohm & Haas). After the end of hydrolysis (GC check), the ion exchanger was removed by filtration and washed with dry methanol.

The combined filtrates were admixed with 5 drops of concentrated phosphoric acid ($H_3PO_4$) and then the solvent was removed on a rotary evaporator at max. 30° C. and 0.5 mbar at the end. The residue obtained was 65.6 g of acrolein cyanohydrin (98% purity by GC and NMR), corresponding to a yield of 97.8% of theory. The resulting acrolein cyanohydrin was used without further purification.

NMR ($CDCl_3$):
$^1H$: 3.97 ppm (s); 5.01 ppm (d); 5.47 ppm (d); 5.63 ppm (d); 5.95 ppm (m);
$^{13}C$: 62.03 ppm; 116.41 ppm; 117.38 ppm; 131.53 ppm.

*The ion exchanger was activated by washing with half-concentrated hydrochloric acid, then with water, and lastly with ethanol. After that the ion exchanger was dried under reduced pressure at 60° C. (the ion exchanger can be used more than once, i.e. used again, for the same reaction).

Example 2: n-Butyl (3-cyano-3-hydroxypropyl)methylphosphinate (ACM-H)

In a stirring apparatus with impeller stirrer, 20 g (0.1445 mol) of mono-n-butyl methanephosphonate (98.5% purity, MPE, corresponding to formula (IIb) with $R^2$=n-butyl) were introduced under nitrogen and heated to 85° C. Added to this initial charge with vigorous stirring was 0.1 g of tert-butyl peroxyneodecanoate (radical initiator of the formula (IV)). Subsequently, the following mixtures were metered in simultaneously from two different syringe pumps: in one syringe pump, a mixture of 5.0 g (0.036 mol) of MPE and 5.1 g of acrolein cyanohydrin (0.058 mol, purity: 94%), and in the other syringe pump a mixture of 15 g (0.1084 mol) of MPE and 0.6 g of tert-butyl peroxyneodecanoate. The total amount of tert-butyl peroxyneodecanoate was therefore 0.003 mol. The simultaneous metered introduction of the two mixtures into the stirring apparatus took place at constant temperature with vigorous stirring over a period of 2.5 hours. The resulting pale yellow reaction mixture, after the end of simultaneous metered introduction of the two mixtures, was stirred at 85° C. for 30 minutes more and then cooled.

According to $^{31}P$ NMR, the reaction mixture contained 21.3 mol % of the desired product (ACM-H) and 78.7 mol % of the MPE reactant.

According to $^1H$ NMR, the reaction mixture no longer contained any acrolein cyanohydrin reactant.

30.0 g of the excess MPE were separated off (for the purpose of re-use as well) via a short-path evaporator distillation (outer jacket temperature of 105° C. and down to a pressure of 0.2 mbar). Remaining in the bottom were 12.5 g of the desired n-butyl (3-cyano-3-hydroxypropyl)methyl-phosphinate product (ACM-H) with a purity of 95% (according to GC and NMR analysis). The yield of ACM-H therefore corresponds to 93.6% of theory, based on acrolein cyanohydrin.

NMR ($CDCl_3$):
$^1H$: 0.95 ppm (t); 1.41 ppm (m); 1.52 ppm (d, d); 1.65 ppm (m); 2.0 ppm (m); 2.1 ppm (m); 4.0 ppm (m); 4.58 ppm (m); 6.15 ppm (s).
$^{31}P$ NMR: 55.5 ppm.

Example 3: n-Butyl (3-cyano-3-hydroxypropyl)methylphosphinate (ACM-H)

The batch size corresponded to that from Example 2, and the reaction procedure was in analogy to Example 2, but using tert-butyl peroxy-2-ethylhexanoate as radical initiator instead of tert-butyl peroxyneodecanoate, and the amount of tert-butyl peroxy-2-ethylhexanoate was 0.04 mol per mole of acrolein cyanohydrin. The reaction temperature was 88° C., the metering time 1.5 hours.

The reaction mixture also contained 3% of the acrolein cyanohydrin reactant. Acrolein cyanohydrin and excess MPE were removed as described above via a short-path evaporator distillation.

The yield of ACM-H found was 90% of theory, based on acrolein cyanohydrin.

Example 4: n-Butyl (3-cyano-3-hydroxypropyl)methylphosphinate (ACM-H)

The batch size corresponded to that from Example 2, and the reaction procedure was in analogy to Example 2, but using a mixture of tert-butyl peroxy-2-ethylhexanoate and tert-butyl peroxyneodecanoate (in each case 0.04 mol per mole of acrolein cyanohydrin) as radical initiator. The reaction temperature was 88° C., the metering time 2 hours. Further work-up was as described above.

The reaction mixture also contained traces of the acrolein cyanohydrin reactant.

The yield of ACM-H found was 93% of theory, based on acrolein cyanohydrin.

Example 5: n-Butyl (3-cyano-3-hydroxypropyl)methylphosphinate (ACM-H)

Apparatus: First stirring vessel with heating jacket, two metering pumps, and bottom drain valve, connected to a second stirring vessel; the stirring vessels were each equipped with an impeller stirrer.

Procedure: Quasi-Continuous Mode

Process Section 1:

In analogy to the experimental description in Example 2, the first stirring vessel was charged with 21 g of MPE under a nitrogen atmosphere, 0.1 g of tert-butyl peroxy-2-ethylhexanoate was added, and the mixture was heated to 88° C. Thereafter, with vigorous stirring, two different syringe pumps supplied metered feeds to this first stirring vessel, the first feed being a mixture of 8.06 g of acrolein cyanohydrin and 11.94 g of MPE, and the other feed being a mixture of 19 g of MPE, 0.93 g of tert-butyl peroxyneodecanoate and 0.7 g of tert-butyl peroxy-2-ethylhexanoate, the feeds taking place at constant temperature over a period of 2 hours.

Process Section 2:

The reaction temperature was held further at 88° C. Subsequently, over a further 2 hours, once again the same amounts of the same two mixtures of acrolein cyanohydrin and MPE and of MPE, tert-butyl peroxyneodecanoate and tert-butyl peroxy-2-ethylhexanoate as described above were metered separately into the first stirring vessel via the same syringe pumps. In addition, a further 21 g of MPE were added dropwise and simultaneously from the first stirring vessel, by slow run-off through the bottom valve, a constant run-off into the second stirring vessel, heated at 80° C., was ensured, and hence a constant fill level in the first reactor was obtained as well.

Process Section 3:

After the end of the metered addition of the two mixtures and of the MPE, process section 2 was repeated once again.

In the reaction mixture subsequently obtained, there was no longer any acrolein cyanohydrin.

For working up, the mixture was purified via a short-path evaporator at a jacket temperature of 115° C., 0.2-0.5 mbar. The excess MPE obtained as distillate (115 g) was used again in later batches.

In the distillation bottom product there remained 58.6 g of n-butyl (3-cyano-3-hydroxypropyl)-methylphosphinate (94.8% crude yield), which could be used directly, i.e. without further purification, in the subsequent reactions, for the preparation, for example, of glufosinate-ammonium.

Example 6: n-Butyl (3-cyano-3-hydroxypropyl)methylphosphinate (ACM-H)

In a jacketed stirring vessel inertized using nitrogen and possessing thermometer, impeller stirrer and a bottom drain valve whose drain led into a heatable flask fitted with stirrer, the initiating reaction was first of all carried out.

Initiating Reaction:

First of all 27 g of MPE were introduced and heated to 76° C. Thereafter 0.1 g of initiator (1,1,3,3-tetramethylbutyl peroxyneodecanoate, acquired commercially as Trigonox® 423) was added. Subsequently, by means of two different syringe pumps, the following mixtures were metered in simultaneously: in one syringe pump, a mixture of 9.7 g (97% purity) of acrolein cyanohydrin and 10.0 g of MPE, and simultaneously, in the other syringe pump, a mixture of 18.0 g of MPE and 2.4 g of Trigonox® 423. The two mixtures were metered in at a uniform rate over 2 hours, the temperature in the jacketed stirring vessel being held at 76° C.

Continuous Reaction Regime:

As described above, two mixtures were metered subsequently into the reaction vessel simultaneously and at a uniform rate over 6 hours, at the same temperature:

Via a first pump, a mixture of 29.1 g of acrolein cyanohydrin and 30 g of MPE, and, via a second pump, a mixture of 54 g of MPE and 7.2 g of Trigonox® 423 were metered into the reaction vessel. Simultaneously over the same period of time, from a third metering vessel, a total of 81 g of MPE were added dropwise at a uniform rate. In order to keep a constant fill level in the reaction vessel, a total of 195 g of the resultant reaction mixture were drained off through the bottom valve into the flask which was maintained at 76° C. and provided with a stirrer, throughout the duration of metering.

The reaction mixture was pale yellow and clear. After an after-reaction time of around 15 minutes, the reaction mixtures were combined. For working up, the low-boiling components (including the excess MPE) were distilled off via a short-path evaporator (0.2 mbar/115° C.). The crude product remaining in the bottom can be used directly in this form for further reactions. 101.8 g of product (the GC purity of ACM-H was 9.15%) were obtained, corresponding to a yield of 94% of theory, based on acrolein cyanohydrin.

Example 7: Ammonium D,L-homoalanin-4-yl(methyl)phosphinate (Glufosinate-Ammonium)

From 218 g (0.885 mol) of n-butyl (3-cyano-3-hydroxypropyl)methylphosphinate (purity: 89%), further reaction was carried out with ammonia and with hydrochloric acid, similarly to the processes described in U.S. Pat. No. 6,359, 162B1 or CN 102399240A. Lastly, ammonia was added, giving an aqueous solution of the ammonium salt.

Obtained in this way were 742.2 g of an aqueous solution containing 22.5% of glufosinate-ammonium, corresponding to a yield of 95.2% of theory.

The invention claimed is:

1. Process for preparing a compound of formula (I)

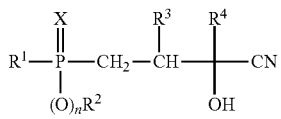  (I)

comprising reacting a compound of formula (II)

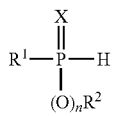  (II)

with a cyanohydrin of formula (III)

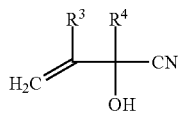  (III)

at a temperature in a range from 50 to 105° C.,
where in each case:
$R^1$ is $(C_1$-$C_{12})$-alkyl, $(C_1$-$C_{12})$-haloalkyl, $(C_6$-$C_{10})$-aryl, $(C_6$-$C_{10})$-haloaryl, $(C_7$-$C_{10})$-aralkyl, $(C_7$-$C_{10})$-haloaralkyl, $(C_4$-$C_{10})$-cycloalkyl or $(C_4$-$C_{10})$-halocycloalkyl,
$R^2$ is $(C_1$-$C_{12})$-alkyl, $(C_1$-$C_{12})$-haloalkyl, $(C_6$-$C_{10})$-aryl, $(C_6$-$C_{10})$-haloaryl, $(C_7$-$C_{10})$-aralkyl, $(C_7$-$C_{10})$-haloaralkyl, $(C_4$-$C_{10})$-cycloalkyl or $(C_4$-$C_{10})$-halocycloalkyl,
$R^3$ and $R^4$ are in each case independently of one another hydrogen, $(C_1$-$C_4)$-alkyl, phenyl or benzyl,
X is oxygen or sulphur, and
n is 0 or 1.

2. Process according to claim 1, wherein the reacting takes place at a temperature in a range from 60 to 95° C.

3. Process according to claim 1, wherein the reacting takes place at a temperature in a range from 65 to 90° C.

4. Process according to claim 1, wherein a compound of formula (IIa)

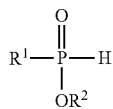  (IIa)

is reacted with an acrolein cyanohydrin of formula (IIIa)

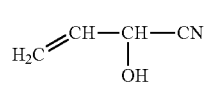  (IIIa)

where:
$R^1$ is $(C_1$-$C_6)$-alkyl, $(C_1$-$C_6)$-haloalkyl, $(C_6$-$C_8)$-aryl, $(C_6$-$C_8)$-haloaryl, $(C_7$-$C_{10})$-aralkyl, $(C_7$-$C_{10})$-haloaralkyl, $(C_5$-$C_8)$-cycloalkyl or $(C_5$-$C_8)$-halocycloalkyl,
$R^2$ is $(C_1$-$C_6)$-alkyl, $(C_1$-$C_6)$-haloalkyl, $(C_6$-$C_8)$-aryl, $(C_6$-$C_8)$-haloaryl, $(C_7$-$C_{10})$-aralkyl, $(C_7$-$C_{10})$-haloaralkyl, $(C_5$-$C_8)$-cycloalkyl or $(C_5$-$C_8)$-halocycloalkyl.

5. Process according to claim 1, wherein the reacting is carried out with aid of a radical-forming radiation source or in the presence of one or more radical-forming substances.

6. Process according to claim 1, wherein the reacting takes place in the presence of one or more radical initiators of formula (IV)

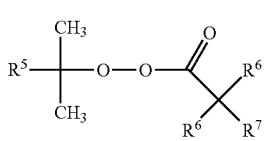  (IV)

where
$R^5$ is methyl, ethyl, 2,2-dimethylpropyl or phenyl,
$R^6$ independently at each occurrence is $(C_1$-$C_{10})$-alkyl and
$R^7$ is hydrogen or $(C_1$-$C_{10})$-alkyl.

7. Process according to claim 6, wherein the reacting takes place in the presence of one or more radical initiators selected from the group consisting of tert-butyl peroxypivalate, tert-amyl peroxypivalate, tert-butyl peroxyneodecanoate, 1,1,3,3-tetramethylbutyl peroxyneodecanoate, tert-butylperoxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, and cumyl peroxypivalate.

8. Process according to claim 6, wherein $R^6$ independently at each occurrence is $(C_1$-$C_4)$-alkyl and $R^7$ is hydrogen or $(C_1$-$C_4)$-alkyl.

9. Process according to claim 1, wherein the molar ratio of the total amount of the phosphorus-containing reactant (II) used to the total amount of the cyanohydrin of the formula (III) used is in a range from 2:1 to 8:1.

10. Process according to claim 6, wherein the radical initiator or initiators of the formula (IV) or a portion of the radical initiators of the formula (IV) is premixed with a portion or the entirety of compound (II), and this mixture is metered into the reaction vessel simultaneously with the compound of the formula (III).

11. Process according to claim 1, wherein $R^1$ is methyl, $R^2$ is n-butyl, $R^3$ and $R^4$ are hydrogen, n is 1 and X is oxygen.

12. Process according to claim 1, further comprising preparing one or more glufosinate and/or glufosinate salts

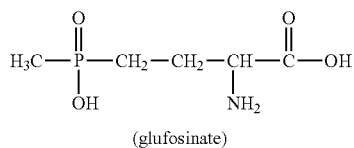

(glufosinate)

wherein the compound of formula (I) comprises a compound of formula (Ib) comprising:
reaction of a compound of the formula (Ib) to give a corresponding compound of formula (V),

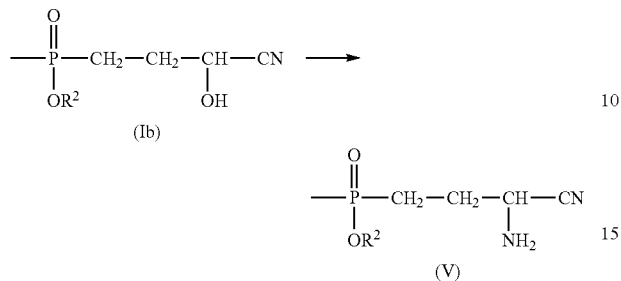

where $R^2$ is in each case either n-butyl or n-pentyl, and reacting a compound of formula (V) to give the glufosinate or a salt thereof.

13. Process according to claim 12, wherein the preparation of compound (V) takes place by reaction of compound (Ib) with $NH_3$.

* * * * *